United States Patent [19]

King

[11] Patent Number: 5,417,973

[45] Date of Patent: May 23, 1995

[54] PROTECTIVE COATING FOR CARCASSES

[76] Inventor: Roger A. King, 146 First Ave., Evanston, Wyo. 82930

[21] Appl. No.: 369,752

[22] Filed: Jun. 22, 1989

[51] Int. Cl.$^6$ .................... A61K 35/78; A01N 25/00
[52] U.S. Cl. .................... 424/195.1; 424/405
[58] Field of Search .................... 424/405, 195.1

[56] References Cited

U.S. PATENT DOCUMENTS

| | | | |
|---|---|---|---|
| 122,608 | 1/1872 | Heins | 424/195.1 |
| 617,956 | 1/1899 | Davenport | 424/195.1 |
| 4,211,577 | 7/1980 | Wallin | 106/288 |
| 4,876,090 | 10/1989 | Weisler | 424/195.1 |

OTHER PUBLICATIONS

Southwest Entomology 15 (2) 1990 Butler G. D., Jr. pp. 123-132.

Kirk-Othmer Encyclopedia of Chemical Technology vol. 9, John Wiley & Sons 1980 pp. 721-737.
Chase et al., *Remington's Pharmaceutical Sciences*, Mack Printing Co., Easton, Pa., pp. 1461-1462.

*Primary Examiner*—William H. Beisner
*Assistant Examiner*—Ralph Gitomer
*Attorney, Agent, or Firm*—Trask, Britt & Rossa

[57] ABSTRACT

Disclosed is a composition for repelling pests (e.g. insects and birds) from an animal carcass. This pest repelling composition contains a repellant (e.g. pepper extract) in admixture with a fluid vehicle, such as a light cooking oil. The repellant is present in a sufficient concentration to repel a pest when it contacts the animal carcass to which the composition has been applied. The composition may also include salt to help preserve the animal. The composition is applied to the exterior of the carcass. Repeated applications may be performed. The invention also includes a process for making the pest repelling composition.

14 Claims, No Drawings

PROTECTIVE COATING FOR CARCASSES

BACKGROUND OF THE INVENTION

1. Field

This invention relates to a composition and method for protecting carcasses, and more particularly, to a liquid coating for repelling insects and other pests from carcasses.

2. State of the Art

Animals such as deer, rabbits, bear, antelope, bison, elk, caribou, moose, bighorn sheep, and others are hunted for their meat, skin, rack, and head. Once the animal has been killed, it is typically gutted and bled, and the dressed meat or carcass is allowed to "cool." Ranchers also allow the carcasses of their livestock to "cool" or "age." Fishermen face the same problem with fish they have caught.

During this cooling process, the meat is susceptible to attack by "blowflies," flies, gnats, yellow jackets, cats, dogs, birds (e.g. "camp robbers") and other pests. These pests can eat substantial portions of the meat (e.g. cats), or can lay eggs on it (e.g. flies).

Various means for preventing such despoliation by pests have been devised. For example, the carcass can be placed in a cheesecloth sack. However, these sacks are generally ineffective, since the flies can still lay eggs through tears in the sack, and animals such as cats can rip through the sack and eat the meat. People have tried to wrap the carcass with sheets, but the carcass does not then cool properly.

Still other people have tried to sprinkle ground pepper onto the carcass to repel pests. This method is only partially effective since the pepper only adheres to moistened portions of the carcass. Furthermore, wind typically blows the pepper away during the cooling process.

It would be an improvement in the art to have an effective, inexpensive way of protecting carcasses during the cooling process.

SUMMARY OF THE INVENTION

The invention includes a composition for repelling pests from an animal carcass. This pest repelling composition contains a repelling agent in admixture with a fluid vehicle.

The repelling agent will be in a sufficient concentration to repel a pest when the pest contacts the animal carcass to which the composition has been applied. "Contact," as used herein, not only means physical contact with the animal carcass, but also smelling, tasting, or otherwise sensing the presence of the composition on the carcass.

Repelling agents (repellants) will generally be agents, non-toxic to man in the amounts used, which repel pests generally, or particular pests specifically. The repelling agent will typically be extracted from a plant part. Plant parts useful in the invention include plant parts of cayenne, capsicum, Piper species (black and white pepper), onion, chives, and garlic.

Fluid vehicles are typically liquid solvents capable of acting as a solvent for the repelling agents found in the plant parts. They should be non-toxic to man in the amounts used. The fluid vehicles should, but need not, have a boiling point greater than about 120 degrees Fahrenheit (48.9 degrees centigrade (C)) so that the composition does not evaporate too quickly. Typical fluid vehicles are liquids oils, such as palm oil, cottonseed oil, corn oil, vegetable oil, olive oil, sesame oil, peanut oil, and mixtures thereof.

The composition will also typically, but need not, include a salt (e.g. sodium or potassium chloride) in admixture with the repelling agent and fluid vehicle. The salt helps to preserve the animal. The presence of salt in combination with the fluid vehicle helps to prevent dehydration. Such an attribute is especially useful if the animal is later to be stuffed or mounted by a taxidermist. The composition can be applied to the areas of the animal which are particularly sensitive to dehydration (e.g. the nose, eyes, and mouth) to prevent dehydration until the animal can be mounted.

The invention also includes a method of preserving and preventing pest damage to an animal carcass or skin. The method is achieved by applying to the carcass exterior a sufficient amount of the aforementioned pest repelling composition to repel the pests. The pest repelling composition may be applied by spray application (e.g. by a pump sprayer or aerosol applicator), brushing, wiping, or other techniques for applying a liquid onto a surface. Application of a thin layer to the entire exposed portion of the carcass is preferred.

After a sufficient amount of time has elapsed to decrease the efficacy of the pest repelling composition (e.g. by evaporation or running) another application of the pest repelling composition may be applied to the animal in a sufficient amount to repel the pests.

The composition can be applied to the entire animal carcass, and adheres to even dry portions of the meat. The composition may also be applied to a fish carcass. Since it is capable of spray application, a small (e.g. 360 ml (12 fl. oz.)) spray bottle of the composition can be taken hunting with a hunter or fisherman. Spray application over the entire carcass protects all portions of the meat from most pests. Twelve ounces will generally cover an entire deer carcass adequately. The composition is non-toxic and does not adversely affect humans.

Certain pests (e.g. cats), if they are especially hungry, may be able to scavenge the carcass even with the composition applied. The composition may, however, still deter even these animals or incline them to look for untreated food elsewhere if it has a sufficiently thick coating of the composition on it.

The invention also includes a process for making a pest repelling composition.

DETAILED DESCRIPTION OF THE PREFERRED EMBODIMENTS

Pepper, the pungent product from the fruit of the East Indian plant *Piper nigrum*, either separately or in conjunction with other agents, contains a preferred repellant for use in the invention. It is commonly known as "black pepper" or "white pepper" and is readily commercially available as "pepper corns" or "ground pepper" under various trademarks (e.g. from Schilling or McCormick of Baltimore, Md.) White pepper is preferred since it leaves less plant material behind after the hereinafter described extraction processes. Other Piper species extractives should also contain a repelling agent.

Concentrations of pepper (Piper species) useful in the composition vary from about one part to about twenty parts of ground pepper per seventy-one parts oil.

Another preferred repellant is derived from capsicum (from the plant *Capsicum frutescens*). The fruit of this plant can be air or kiln dried and then extracted for its repellant.

Other preferred agents include extractives of the various varieties of onion (*Allium cepa*), garlic (*Allium sativum*), and chive (*Allium schoenoprasum*). These plants and their bulbs are readily available from most food markets.

The various plant parts may be first dried, and an extractive made. Methods for extraction, and various extractives, definitionally, are described in Chase et al. *Remington's Pharmaceutical Sciences*, Mack Printing Co., Easton, Pa. (16th ed. 1980) at pages 1461–1462, the contents of which are incorporated by this reference.

In the cases of Cayenne and Piper species extractions, an organic, as opposed to a polar, extractive is preferred since organic extractives appear to contain a repelling agent useful in the invention.

The fluid vehicles of the composition are preferably non-toxic in the amounts used; are able to act as a vehicle for the particular repelling agent (e.g. have the proper polarity); and have a boiling point sufficiently high that the composition will not evaporate too rapidly from the carcass. Preferred vehicles include various light cooking oils such as palm oil, safflower oil, cottonseed oil, corn oil, vegetable oil, olive oil, sesame oil, peanut oil, and combinations thereof.

The fluid vehicle is preferably also used in the extraction process to save processing steps. However, an alcohol (e.g. ethanol) or other solvent extraction of the repellant from the plant matter and subsequent admixture of the extract with the chosen fluid vehicle will also suffice.

Additional details of the invention will appear from the following examples in conjunction with the claims.

EXAMPLES

Example A

A composition for repelling pests was made according to the following recipe.

Three (3) teaspoons (15 cc) of ground white pepper, two (2) teaspoons (10 cc) of dried red cayenne, and one (1) teaspoon (5 cc) of Tenderquick ® fine ground salt (Morton of Chicago, Ill.) wrapped in a cheesecloth were placed in 12 fluid ounces (360 ml) of cottonseed oil contained within a cooking pot.

The cooking pot was heated until the mixture began to boil. The temperature was decreased, and the mixture was allowed to simmer just below the boiling point of the cottonseed oil for one-half hour. The mixture was then set aside to cool and the boiled materials (e.g. salt sack and pepper plant parts) were allowed to settle. The top portion of the mixture was drawn off. Alternatively, it could have been siphoned, decanted, poured, or filtered (e.g. through cheesecloth) to separate the pest repelling composition.

The drawn off or extracted portion was later applied to beef scraps and a deer carcass which was cooling. Flies, gnats, yellow jackets, and j"camp robbers" approached the meat, but after contacting it, did not eat or despoil it.

Example B

A composition similarly effective to the composition of Example A can be made by substituting two tablespoons (30 cc) of dried onion flakes for the pepper and cayenne of Example A.

Examples C and D

A similarly effective composition can be made by substituting corn oil for cottonseed oil in the composition of Example A or B.

Example E and F

The compositions of Examples A–D can also be applied to the carcass of the animal by brush or hand application (e.g. wiping), it only being important that the desired portion of the animal have a sufficiently thick application on the carcass to repel the pests.

Reference herein to specific embodiments and examples is not intended to limit the scope of the appended claims which define the invention.

I claim:

1. A method of limiting damage to an animal carcass caused by potential scavengers, said method comprising:

providing a pest repelling composition comprising a fluid vehicle in admixture with a liquid pungent material derived from a plant source; and applying said pest repelling composition to the exposed surface of an animal carcass to provide an irritative layer preventing contact between pests and said exposed surface.

2. The method according to claim 1, wherein said pungent material is an extract of a plant of the Piper species, said fluid vehicle is an oil selected from the group consisting of palm oil, corn oil, cottonseed oil, peanut oil, olive oil, sesame oil, and combinations thereof, said pest repelling composition being applied by spraying onto said carcass.

3. The method according to claim 1, wherein said pungent material is a liquid extract of a plant of the Piper species, said fluid vehicle is an oil selected from the group consisting of palm oil, corn oil, cottonseed oil, peanut oil, olive oil, sesame oil, and combinations thereof, said pest repelling composition being applied by brushing onto said carcass.

4. The method according to claim 3 further comprising reapplying said pest repelling composition.

5. A process for making a pest repelling composition, said process comprising:

placing from about one part to about twenty parts of plant matter containing a pungent component in about seventy-one parts of a fluid vehicle capable of acting as a solvent for said pungent component to form an admixture;

heating said admixture of plant matter and fluid vehicle to a boil;

lowering the temperature of said admixture to a simmer;

simmering the admixture for about one half hour;

cooling said admixture to room temperature further allowing said plant matter to settle to the bottom of the admixture; and removing from the top of the admixture a pest repelling composition, comprising pungent material in admixture with the fluid vehicle, leaving the majority of the plant matter behind.

6. The process according to claim 5, wherein said fluid vehicle is an oil selected from the group of oils consisting of palm oil, corn oil, cottonseed oil, peanut oil, olive oil, sesame oil, and combinations thereof.

7. The process according to claim 6, wherein said plant matter comprises plant parts selected from the group of plants consisting of cayenne, capsicum, Piper species, onion, chives, garlic, and mixtures and extracts thereof.

8. The process according to claim 7, wherein a packet containing one part inorganic of salt is also placed in the admixture before heating.

9. The process according claim 8, wherein said pest repelling composition is removed from the admixture by siphoning the top of the admixture.

10. The process according to claim 8, wherein said pest repelling composition is removed from the admixture by decanting the admixture, leaving the sediment behind in the lower liquid layers.

11. The process according to claim 8, wherein said pest repelling composition is separated from the remainder of the admixture by filtering the admixture and removing the pest repelling composition as a filtrate.

12. The process according to claim 11, wherein said composition is filtered through cheesecloth.

13. A composition to provide an irritative protective coating for repelling pests from a carcass of an animal, said composition comprising:
   cottonseed oil as a fluid vehicle;
   an inorganic salt; and
   a liquid pungent repelling agent derived from Piper species.

14. The composition of claim 13 wherein said liquid pungent repelling agent is a liquid extract comprising white pepper and cayenne.

* * * * *